United States Patent [19]

Fuchs et al.

[11] Patent Number: 5,068,241
[45] Date of Patent: Nov. 26, 1991

[54] PESTICIDAL SUBSTITUTED PYRAZOLINE DERIVATIVES, COMPOSITIONS AND USE

[75] Inventors: Rainer Fuchs, Wuppertal; Christoph Erdelen, Leichlingen, both of Fed. Rep. of Germany; Benedikt Becker, Appiano, Italy; Wilhelm Stendel, Wuppertal, Fed. Rep. of Germany

[73] Assignee: Bayer Aktiengesellschaft, Leverkusen, Fed. Rep. of Germany

[21] Appl. No.: 652,169

[22] Filed: Feb. 7, 1991

[30] Foreign Application Priority Data

Feb. 17, 1990 [DE] Fed. Rep. of Germany ....... 4005114

[51] Int. Cl.$^5$ ................... A01N 43/56; C07D 231/06
[52] U.S. Cl. ..................................... 514/403; 424/45; 424/46; 548/371; 548/372; 548/379
[58] Field of Search ...................... 548/371, 372, 379; 514/45, 46, 403

Primary Examiner—Robert W. Ramsuer
Attorney, Agent, or Firm—Sprung Horn Kramer & Woods

[57] ABSTRACT

Pesticidal substituted pyrazoline derivatives of the formula

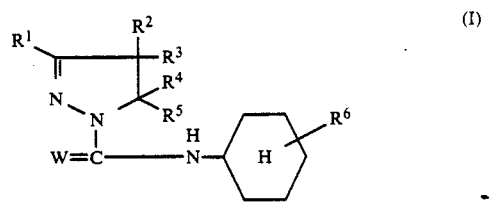

in which
$R^1$ represents optionally substituted phenyl or optionally substituted alkyl,
$R^2$ represents hydrogen, optionally substituted phenyl, optionally substituted alkyl or alkoxycarbonyl,
or $R^1$ and $R^2$ together represent an optionally benzo-fused alkylene radical,
$R^3$ represents hydrogen or alkyl,
$R^4$ represents hydrogen, optionally substituted phenyl or optionally substituted alkyl,
$R^5$ represents hydrogen or optionally substituted alkyl,
$R^6$ represents halogenoalkyl or halogenoalkoxy, and
W represents oxygen or sulphur.

13 Claims, No Drawings

PESTICIDAL SUBSTITUTED PYRAZOLINE DERIVATIVES, COMPOSITIONS AND USE

The invention relates to new substituted pyrazoline derivatives, to a process for their preparation, and to their use as pesticides.

It is known that certain substituted pyrazoline derivatives have a good activity against animal pests. In this context see, for example, DE-A 2,700,258, U.S. Pat. No. 4,174,393, DE-A 2,529,689, U.S. Pat. No. 4,070,365.

However, the level, or duration, of action of these previously known compounds is not entirely satisfactory in all fields of application, in particular against certain organisms or when low concentrations are applied.

New substituted pyrazoline derivatives of the general formula (I)

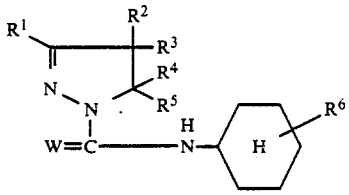

have been found, in which
R$^1$ represents optionally substituted phenyl or optionally substituted alkyl,
R$^2$ represents hydrogen, optionally substituted phenyl, optionally substituted alkyl or alkoxycarbonyl,
or R$^1$ and R$^2$ together represent an optionally benzo-fused alkylene radical,
R$^3$ represents hydrogen or alkyl,
R$^4$ represents hydrogen, optionally substituted phenyl or optionally substituted alkyl,
R$^5$ represents hydrogen or optionally substituted alkyl,
R$^6$ represents halogenoalkyl or halogenoalkoxy, and
W represents oxygen or sulphur.

Furthermore, it has been found that the new substituted pyrazoline derivatives of the general formula (I)

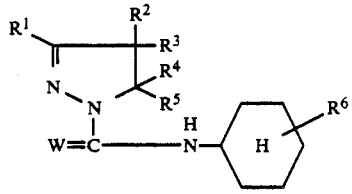

in which
R$^1$ represents optionally substituted phenyl or optionally substituted alkyl,
R$^2$ represents hydrogen, optionally substituted phenyl, optionally substituted alkyl or alkoxycarbonyl, or R$^1$ and R$^2$ together represent an optionally benzo-fused alkylene radical,
R$^3$ represents hydrogen or alkyl,
R$^4$ represents hydrogen, optionally substituted phenyl or optionally substituted alkyl,
R$^5$ represents hydrogen or optionally substituted alkyl,
R$^6$ represents halogenoalkyl or halogenoalkoxy, and
W represents oxygen or sulphur, are obtained when pyrazoline derivatives of the formula

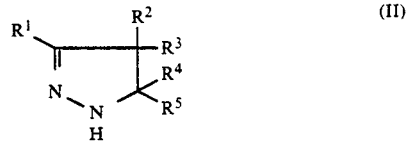

in which
R$^1$, R$^2$, R$^3$, R$^4$ and R$^5$ have the abovementioned meanings, are reacted with isocyanates or isothiocyanates of the formula (III)

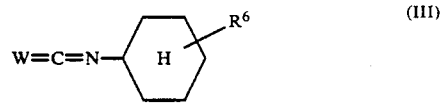

in which
W and R$^6$ have the abovementioned meanings, if appropriate in the presence of bases.

Finally, it has been found that the new pyrazoline derivatives of the general formula (I) have a very good activity against pests and, in particular, a very good insecticidal and acaricidal activity.

Surprisingly, the substituted pyrazoline derivatives according to the invention show a considerably better insecticidal activity against insects and arachnids which damage plants and parasitize warm-blooded animals than compounds which are known from the prior art and which are known chemically and from the point of view of their action.

Formula (I) provides a general definition of the substituted pyrazoline derivatives according to the invention. Preferred compounds of the formula (I) are those in which
R$^1$ represents phenyl which is optionally substituted by halogen, nitro, alkyl(C$_1$-C$_6$), alkoxy(C$_1$-C$_6$), halogenoalkyl(C$_1$-C$_6$), halogenoalkoxy(C$_1$-C$_6$), alkyl(C$_1$-C$_6$)sulphonyl or halogenoalkyl(C$_1$-C$_6$)sulphonyl, or represents alkyl(C$_1$-C$_6$) which is optionally substituted by halogen, alkoxy(C$_1$-C$_6$) or halogenoalkoxy(C$_1$-C$_6$),
R$^2$ represents hydrogen, or phenyl which is optionally substituted by halogen, nitro, alkyl(C$_1$-C$_6$), alkoxy(C$_1$-C$_6$), (C$_1$-C$_6$), halogenoalkyl(C$_1$-C$_6$), halogenoalkoxy(C$_1$-C$_6$), alkyl(C$_1$-C$_6$)sulphonyl or halogenoalkyl(C$_1$-C$_6$)sulphonyl, or represents alkyl(C$_1$-C$_6$) which is optionally substituted by halogen, alkoxy(C$_1$-C$_6$) or halogenoalkoxy(C$_1$-C$_6$), or represents alkoxy(C$_1$-C$_6$)carbonyl,
R$^3$ represents hydrogen or alkyl(C$_1$-C$_6$),
R$^4$ represents hydrogen, or phenyl which is optionally substituted by halogen, alkoxy(C$_1$-C$_4$), alkyl(C$_1$-C$_4$), halogenoalkyl(C$_1$-C$_4$) or halogenoalkoxy(C$_1$-C$_4$), or represents alkyl(C$_1$-C$_6$) which is optionally substituted by halogen or alkoxy(C$_1$-C$_4$),
R$^5$ represents hydrogen or alkyl(C$_1$-C$_6$) which is optionally substituted by halogen or alkoxy(C$_1$-C$_4$),
R$^6$ represents halogenoalkyl(C$_1$-C$_6$) or halogenoalkoxy(C$_1$-C$_6$) and
W represents oxygen or sulphur.

Particularly preferred compounds of the formula those in which

R$^1$ represents phenyl which is optionally substituted by fluorine, chlorine, bromine, nitro, alkyl(C$_1$-C$_4$), alkoxy(C$_1$-C$_4$), halogenoalkyl(C$_1$-C$_4$), halogenoalkoxy(C$_1$-C$_4$), alkyl(C$_1$-C$_4$)sulphonyl, halogenoalkyl(C$_1$-C$_4$)sulphonyl or halogenoalkoxy(C$_1$-C$_4$)sulphonyl, or represents alkyl(C$_1$-C$_4$) which is optionally substituted by fluorine, chlorine, bromine, alkoxy(C$_1$-C$_4$) or halogenoalkoxy(C$_1$-C$_4$), R$^2$ represents hydrogen, or phenyl which is optionally substituted by fluorine, chlorine, bromine, nitro, alkyl(C$_1$-C$_4$), alkoxy(C$_1$-C$_4$), halogenoalkyl(C$_1$-C$_4$), halogenoalkoxy(C$_1$-C$_4$), alkyl(C$_1$-C$_4$)sulphonyl or halogenoalkyl(C$_1$-C$_4$)sulphonyl, or represents alkyl(C$_1$-C$_4$) which is optionally substituted by fluorine, chlorine, bromine, alkoxy(C$_1$-C$_4$) or halogenoalkoxy(C$_1$-C$_4$), or represents alkoxy(C$_1$-C$_4$)carbonyl, R$^3$ represents hydrogen or alkyl(C$_1$-C$_4$), R$^4$ represents hydrogen, or phenyl which is optionally substituted by fluorine, chlorine, bromine, methoxy, ethoxy, methyl, ethyl, halogenoalkyl(C$_1$-C$_2$) or halogenoalkoxy(C$_1$-C$_2$), or represents alkyl(C$_1$-C$_4$) which is optionally substituted by fluorine, chlorine, bromine, methoxy or ethoxy, R$^5$ represents hydrogen, or alkyl(C$_1$-C$_4$) which is optionally substituted by fluorine, chlorine, bromine, methoxy or ethoxy, R$^6$ represents halogenoalkyl which has 1 to 4 carbon atoms and 1 to 7 identical or different halogen atoms from the series comprising fluorine, chlorine and bromine, or represents halogenoalkoxy which has 1 to 4 carbon atoms and 1 to 7 identical or different halogen atoms from the series comprising fluorine, chlorine and bromine, and W represents oxygen or sulphur.

Particularly preferred compounds of the formula (I) are those in which

R$^1$ represents phenyl which is optionally substituted by fluorine, chlorine, bromine, nitro, methyl, ethyl, methoxy, ethoxy, halogenoalkyl which has 1 to 4 carbon atoms and 1 to 7 identical or different halogen atoms from the series comprising fluorine, chlorine and bromine, or by halogenoalkoxy which has 1 to 4 carbon atoms and 1 to 7 identical or different halogen atoms from the series comprising fluorine, chlorine and bromine, or by alkyl(C$_1$-C$_2$)sulphonyl, halogenoalkyl(C$_1$-C$_2$)sulphonyl which has 1 or 2 carbon atoms and 1 to 5 identical or different halogen atoms from the series comprising fluorine, chlorine and bromine, or by halogenoalkoxy(C$_1$-C$_2$)sulphonyl which has 1 or 2 carbon atoms and 1 to 5 identical or different halogen atoms from the series comprising fluorine, chlorine and bromine, or represents alkyl(C$_1$-C$_3$) which is optionally substituted, by fluorine, chlorine, methoxy, ethoxy or halogenoalkoxy(C$_1$-C$_2$) which has 1 or 2 carbon atoms and 1 to 5 identical or different halogen atoms from the series comprising fluorine, chlorine and bromine, R$^2$ represents hydrogen, or phenyl which is optional substituted by fluorine, chlorine, bromine, nitro, methyl, ethyl, methoxy, ethoxy, halogenoalkyl which has 1 to 4 carbon atoms and 1 to 5 identical or different halogen atoms from the series comprising fluorine, chlorine and bromine, or by halogenoalkoxy which has 1 to 4 carbon atoms and 1 to 7 identical or different halogen atoms from the series comprising fluorine, chlorine and bromine, or by alkyl(C$_1$-C$_3$)sulphonyl or halogenoalkyl(C$_1$-C$_3$)sulphonyl; or represents alkyl(C$_1$-C$_3$) which is optionally substituted by fluorine, chlorine, bromine, methoxy, ethoxy or halogenoalkoxy which has 1 to 4 carbon atoms and 1 to 7 identical or different halogen atoms from the series comprising fluorine, chlorine and bromine, or represents alkoxy(C$_1$-C$_3$)carbonyl, R$^3$ represents hydrogen, methyl or ethyl, R$^4$ represents hydrogen, or phenyl which is optionally substituted by fluorine, chlorine, methoxy, ethoxy, methyl, ethyl, halogenoalkyl which has 1 or 2 carbon atoms and 1 to 5 identical or different halogen atoms from the series comprising fluorine, chlorine and bromine, or by halogenoalkoxy which has 1 or 2 carbon atoms and 1 to 5 identical or different halogen atoms from the series comprising fluorine, chlorine and bromine, or represents alkyl(C$_1$-C$_3$) which is optionally substituted by fluorine, chlorine, bromine, methoxy or ethoxy, R$^5$ represents hydrogen, or alkyl(C$_1$-C$_3$) which is optionally substituted by fluorine, chlorine, methoxy or ethoxy, and R$^6$ represents trifluoromethyl, chloro-difluoromethyl, 2,2,2-trifluoroethyl, pentafluoroethyl, difluoromethyl, 1,2,2,2-tetrafluoroethyl, 1,1,2,3,3,3-hexafluoropropyl, trifluoromethoxy, chloro-difluoromethoxy, 2,2,2-trifluoroethoxy, pentafluoroethoxy, difluoromethoxy, 1,2,2,2-tetrafluoroethoxy, or 1,1,2,3,3,3-hexafluoropropoxy.

If, for example, 3,4-bis-(4-chlorophenyl)-4,5-dihydropyrazole and 4-trifluoromethylcyclohexyl isocyanate are used as starting substances, the course of the reaction can be illustrated as follows:

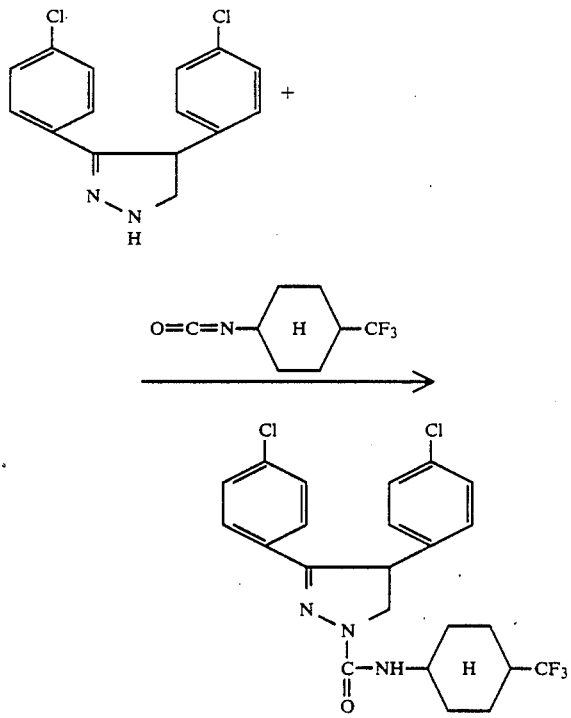

Formula (II) provides a general definition of the pyrazoline derivatives used as starting substances for carrying out the process according to the invention. In this formula (II), $R^1$, $R^2$, $R^3$, $R^4$ and $R^5$ preferably represent those radicals which are already mentioned in connection with the description of the substances of the formula (I) according to the invention as being preferred for these substituents.

The pyrazoline derivatives of the formula (II) are known or can be prepared by methods known per se. In this context, see J. Agric. Food Chem. Vol. 25, No. 5, (1977) p. 987, J. Agric. Food Chem. Vol. 27, No. 2, (1979), p. 406, J. Agric. Food Chem. Vol. 26, No. 4, (1978), p. 915, U.S. Pat. No. 4439,440; EP-A 113,213; EP-A 058,424; U.S. Pat. No. 4,663,341; DE-A 3,628,647; EP-A 286,346.

Formula (III) provides a general definition of the isocyanates or thioisocyanates employed as starting compounds in the process according to the invention. In this formula (III), W and $R^6$ preferably represent those radicals which are already mentioned in connection with the description of the substances of the formula (I) according to the invention as being preferred for these substituents. The compounds of the formula (III) are known or can be prepared by methods known per se. In this context, see DE-A 2,528,162.

The reaction of compounds of the formula (II) with compounds of the formula (III) is preferably reacted in an organic solvent or solvent mixture at temperatures of from 0° to 150° C., preferably at 20° to 90° C. Organic solvents which are suitable are all those which are inert in the reaction, ethers such as diethyl ether, tetrahydrofuran or diisopropyl ether, or nitriles such as acetonitrile, preferably being employed. The process can be carried out at atmospheric pressure or under elevated pressure, the reaction preferably being carried out under atmospheric pressure. If appropriate, the reaction is carried out in the presence of organic or inorganic bases. Organic bases which are preferably suitable are amines such as triethylamine, trimethylamine, diethylamine, aniline, methylaniline, dimethylamine, etc. Inorganic bases which can be employed are all customary inorganic bases such as NaOH, KOH, $Na_2CO_3$, $NaHCO_3$, $K_2CO_3$, ammonia, etc. The reactants of the compounds of the formula (II) and compounds of the formula (III) are preferably employed in equimolar ratios, but it is also possible to add an excess, preferably a small excess, of a reactant.

The reaction products are worked up by methods which are customary per se.

The active compounds are suitable for combating animal pests, preferably arthropods and nematodes, in particular insects and arachnids, which are encountered in agriculture, in animal keeping, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber*. From the order of the Diplopoda, for example, *Blaniulus guttulatus*. From the order of the Chilopoda, for example, *Geophilus carpophagus* and *Scutigera spec*. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria*. From the order of the Dermaptera, for example, *Forficula auricularia*. From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lecularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp. Psylla spp*. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella, Agrotis spp., Euxoa spp., Feltia spp., Earias insulana,* Heliothis spp., *Spodoptera exigua, Mamestra brassicae, Panolis flammea, Prodenia litura,* Spodoptera spp., Trichoplusia ni, *Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*. From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varive stis,* Atomaria spp., i Oryzaephilus surinamensis, Antho nomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Cono derus spp., *Melolontha melolontha, Amphimallon solsti tialis* and *Costelytra zealandica*. From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Hydrotaea spp., Haematobia spp., Glossina spp., Melophagus spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa*.

From the order of the Siphonaptera, for example, *Xenopsylla cheopis,* Ceratophyllus spp. and Ctenocephalides spp. From the order of the Arachnida, for example, Scorpio maurus and Latrodectus mactans.

From the order of the Acarina, for example,

Argas spp., Ornithodoros spp., *Dermanyssus gallinae,* Ornithonyssus spp., *Eriophyes ribis, Phyllocoptruta oleivora,* Boophilus spp., Rhipcephalus spp., Amblyomma spp., Hyalomma spp., Ixodes spp., Dermacentor spp., Haemaphysalis spp., Otobius spp., Psoroptes spp., Chorioptes spp., Sarcoptes spp., Psorergates spp., Demodex spp., Notoedres spp., Tarsonemus spp., Bryobia praetiosa, Panonychus spp. and Tetranychus spp.

The active compounds according to the invention are not only active against plant, hygiene and stored-product pests, but also, in the veterinary medicine sector, against animal parasites (ectoparasites and endoparasites) such as scaly ticks, argasidae, scab mites, trombidae, flies (stinging and licking), parasitic fly larvae, lice, hair lice, bird lice, fleas, and worms which live as endoparasites.

They are active against normally-sensitive and resistant species and strains and against all parasitic and non-parasitic stages of development of the ecto- and endoparasites.

The active compounds according to the invention are distinguished by a powerful insecticidal and acaricidal activity.

They can be employed with particularly good success for combating insects which damage plants, such as, for example, against the green peach aphid (*Myzus persicae*) or against the larvae of the mustard beetle (*Phaedon cochleariae*) or against the larvae of the cabbage moth (*Plutella xylostella*) or against the larvae of the green rice leafhopper (*Nephotettix cincticeps*) or against the larvae of the cotton boll worm (*Heliothis armigera*) or against the larvae of the armyworm (*Spodoptera frugiperda*); and for combating mites which damage plants such as, for example, against the common spider mite or the greenhouse red spider mite (*Tetranychus urticae*).

In addition, they can be employed with particularly good success for combating pests which live as parasites on warm-blooded animals such as, for example, against the larvae of the sheep maggot fly (*Lucilia cuprina*), against cattle ticks (*Boophilus microplus*) or against scab mites (*Psoroptes ovis*) and against cockroaches (*Blattella germanica* and others).

Moreover, the compounds according to the invention show an activity against parasitic protozoa, namely, in particular, against Coccidia and/or Plasmodium.

The active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals as well as granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations or in the use forms prepared from these formulations as a mixture with other known active compounds, such as insecticides, attractants, sterilants, acaricides, nematicides, fungicides, growth-regulating substances or herbicides. The insecticides include, for example, phosphoric esters, carbamates, carboxylic esters, chlorinated hydrocarbons, phenylureas, substances produced by microorganisms, and others.

The active compounds according to the invention can furthermore be present in their commercially available formulations and in the use forms prepared from these formulations as a mixture with synergists. Synergists are compounds by which the action of the active compounds is increased without it being necessary for the synergist added to be active itself.

The active compound content of the use forms prepared from the commercially available formulations can vary within wide limits. The active compound concentration of the use forms can be from 0.0000001 up to 95

% by weight of active compound, preferably between 0.0001 and 1% by weight.

Application is effected in a customary manner which is selected to suit the use forms.

When applied against hygiene pests and pests of stored products, the active compounds are distinguished by an outstanding residual action on wood and clay and by a good stability to alkali on limed substrates.

The active compounds according to the invention are also suitable for combating insects, mites, ticks etc. in the field of animal keeping and livestock breeding, it being possible to achieve better results, for example higher milk yields, higher weight, more attractive animal pelt, longer life, etc., by combating the pests.

The active compounds according to the invention are applied in a manner known in this field, such as by external application, for example in the form of dipping, spraying, pouring-on and spotting-on, and powdering, as well as by parenteral administration, for example in the form of an injection, and furthermore by the feed-through method. In addition, they can also be applied as shaped articles (collar, ear tag) or in the form of the so-called environment treatment.

The biological activity of the compounds according to the invention will be illustrated with the aid of Examples A, B and C.

PREPARATION EXAMPLES

Example 1

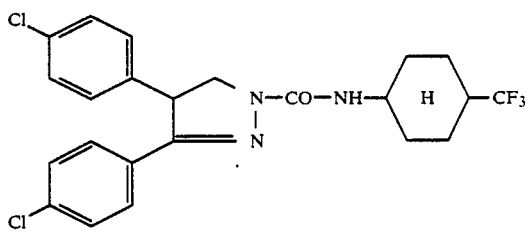

14.5 g (0.05 mol) of 3,4-bis-(4-chlorophenyl)-4,5-dihydropyrazole are dissolved in 160 ml of anhydrous diethyl ether, 9.7 g of cis-trans-4-trifluoromethylcyclohexyl isocyanate are added, and 3 drops of triethylamine are added, with stirring. The stirred mixture is then refluxed for 30 minutes. The reaction mixture is then allowed to stand for 10 hours at room temperature, and the crystals which have precipitated are then filtered off with suction. In this manner, 8.1 g of an isomer of N-4-trifluoromethylcyclohexyl-3,4-bis-(4-chlorophenyl)-4,5-dihydro-1-pyrazolecarboxamide are obtained as colorless crystals of melting point 178° C.

Example 2

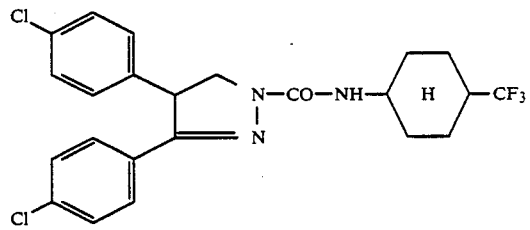

14.5 g (0.05 mol) of 3,4-bis-(4-chlorophenyl)-4,5-dihydropyrazole are dissolved in 20 ml of anhydrous acetonitrile, and 9.7 g of cis/trans-4-trifluoromethylcyclohexyl isocyanate are added, with stirring. The mixture is heated to 50° C., and 2 drops of triethylamine are then added. The mixture is subsequently stirred at 50° C. for half an hour. When the mixture has cooled, the solvent is distilled off in vacuo. 24 g of cis/trans-N-4-trifluoromethylcyclohexyl-3,4-bis-(4-chlorophenyl)-4,5-dihydro-1-pyrazolecarboxamide are obtained as a yellow oil.

$^1$H-NMR (CDCl$_3$, TMS, ppm):7.52–7.09 (8H, m) 6.22 and 5.93 (1H, 2×d); 4.6–4.7 (1H, m), 4.3–4.42 (1H, m), 3.95–4.01 (1H, m); 4.05–4.14 and 3.65–3.8 (1H, 2×d); 1.25–2.32 (9H, m).

The following compounds can be obtained analogously to Examples 1 and 2:

General formula:

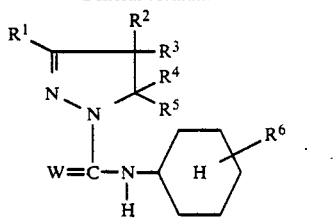

| Example No. | R$^1$ | R$^2$ | R$^3$ | W | R$^4$ | R$^5$ | R$^6$ | M.p. |
|---|---|---|---|---|---|---|---|---|
| 3 | —⟨⟩—OCHF$_2$ | —⟨⟩ | H | O | H | H | 4-CF$_3$ | 145° C. |
| 4 | —⟨⟩—Cl | —⟨⟩—Cl | H | O | H | H | 3-CF$_3$ | 140° C. |
| 5 | —⟨⟩—F | —⟨⟩—F | H | O | H | H | 3-CF$_3$ | Oil |

-continued

| Example No. | R¹ | R² | R³ | W | R⁴ | R⁵ | R⁶ | M.p. |
|---|---|---|---|---|---|---|---|---|
| 6 | 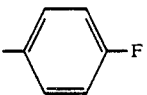 4-F-C₆H₄ | 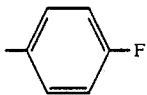 4-F-C₆H₄ | H | O | H | H | 4-CF₃ | Oil |
| 7 | 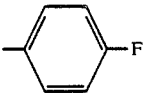 4-F-C₆H₄ | 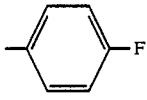 4-F-C₆H₄ | H | S | H | H | 4-CF₃ | Oil |
| 8 | 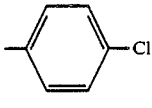 4-Cl-C₆H₄ | 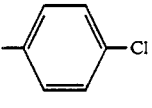 4-Cl-C₆H₄ | H | S | H | H | 4-CF₃ | Oil |
| 9 | 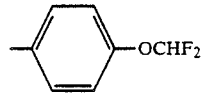 4-OCHF₂-C₆H₄ | 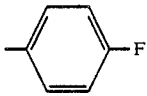 4-F-C₆H₄ | H | O | H | H | 4-CF₃ | Oil |
| 10 | 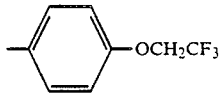 4-OCH₂CF₃-C₆H₄ | 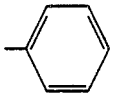 C₆H₅ | H | O | H | H | 4-CF₃ | |
| 11 | 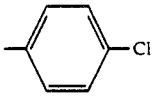 4-Cl-C₆H₄ | 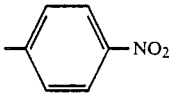 4-NO₂-C₆H₄ | H | O | H | H | 4-CF₃ | |
| 12 | 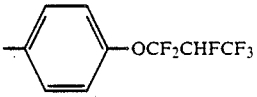 4-OCF₂CHFCF₃-C₆H₄ | 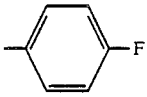 4-F-C₆H₄ | H | O | H | H | 4-CF₃ | |
| 13 | 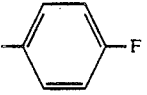 4-F-C₆H₄ | 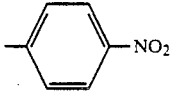 4-NO₂-C₆H₄ | H | O | H | H | 4-CF₃ | |
| 14 | 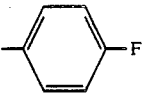 4-F-C₆H₄ | 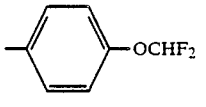 4-OCHF₂-C₆H₄ | H | O | H | H | 4-CF₃ | |
| 15 | 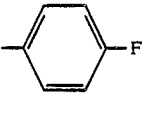 4-F-C₆H₄ | 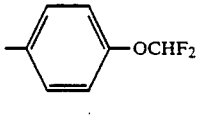 4-OCHF₂-C₆H₄ | H | S | H | H | 4-CF₃ | |
| 16 | 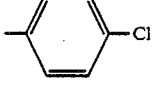 4-Cl-C₆H₄ | 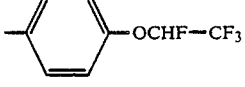 4-OCHF-CF₃-C₆H₄ | H | O | H | H | 4-CF₃ | |
| 17 | 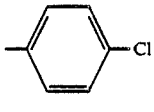 4-Cl-C₆H₄ | 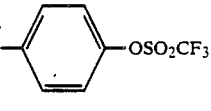 4-OSO₂CF₃-C₆H₄ | H | O | H | H | 4-CF₃ | |
| 18 | 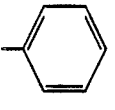 C₆H₅ | 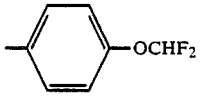 4-OCHF₂-C₆H₄ | H | O | H | H | 4-CF₃ | |

-continued

| Example No. | R¹ | R² | R³ | W | R⁴ | R⁵ | R⁶ | M.p. |
|---|---|---|---|---|---|---|---|---|
| 19 | 4-Br-C₆H₄- | C₆H₅- | H | O | H | H | 4-CF₃ | |
| 20 | tert.-C₄H₉ | H | H | O | H | H | 4-CF₃ | Oil |
| 21 | 4-Cl-C₆H₄- | COOCH₃ | CH₃ | O | H | H | 4-CF₃ | |
| 22 | 4-CF₃-C₆H₄- | COOCH₃ | CH₃ | O | H | H | 4-CF₃ | |
| 23 | 4-Cl-C₆H₄- | H | H | O | H | H | 4-CF₃ | 154° C. |
| 24 | 4-F-C₆H₄- | H | H | O | H | H | 4-CF₃ | |
| 25 | 4-F-C₆H₄- | 4-F-C₆H₄- | H | O | H | H | 4-O—CH₂—CF₃ | oil |
| 26 | 4-Cl-C₆H₄- | 4-Cl-C₆H₄- | H | O | H | H | 4-O—CH₂—CF₃ | |
| 27 | 4-OCHF₂-C₆H₄- | C₆H₅- | H | O | H | H | 4-O—CH₂—CF₃ | |
| 28 | 4-Cl-C₆H₄- | 4-Cl-C₆H₄- | H | O | CH₃ | CH₃ | 4-CF₃ | |
| 29 | 4-F-C₆H₄- | H | H | O | 4-Cl-C₆H₄- | H | 4-CF₃ | |

Use Examples

In the Use Examples which follow, the compound listed below was employed as comparison substance:

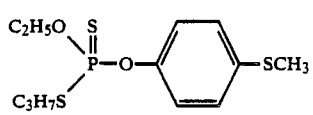

Merpafos=O-ethyl S-propyl O-(4-methylmercaptophenyl)-thionophosphate

EXAMPLE A

Phaedon larvae test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with beetle larvae (*Phaedon cochleariae*), while the leaves are still moist.

After the specified period of time, the destruction in % is determined. 100% means that all the beetle larvae have been killed; 0% means that none of the beetle larvae have been killed.

In this test, a superior activity compared with the prior art is shown, for example, by the following compounds of the Preparation Examples: (1), (6), (7) and (8).

EXAMPLE B

LD$_{100}$ test

| Test animals: | *Sitophilus granarius* |
|---|---|
| Solvent: | 35 parts by weight of ethylene glycol monomethyl ether |
| | 35 parts by weight of nonylphenol polyglycol ether |

To produce a suitable formulation, three parts by weight of active compound are mixed with seven parts by weight of the solvent/emulsifier mixture stated above, and the resulting emulsion concentrate is diluted with water to the concentration desired in each case.

2 ml of this preparation of active compound are pipetted onto filter paper dishes (diameter 9.5 cm) which are located in Petri dishes of the appropriate size. After the filter disc has dried, about 30 test animals are transferred into the Petri dishes, which are covered.

The condition of the test animals is checked 3 days after the experiment has been set up. The time which is required for 100 % knock-down action is determined. If the LD$_{100}$ is not reached after 6 hours, the percentage of the knocked-down test animals is determined.

In this test, for example the compounds of Preparation Examples (3) and (5) showed an LD$_{100}$ of 100 minutes at an exemplary concentration of 1000 ppm of a.i.

EXAMPLE C

Test with *Lucilia cuprina* res. larvae

| Emulsifier: | 35 parts by weight of ethylene glycol monomethyl ether |
|---|---|
| | 35 parts by weight of nonylphenol polyglycol ether |

To produce a suitable preparation of active compound, three parts by weight of active compound are mixed with seven parts by weight of the abovementioned mixture and the concentrate thus obtained is diluted with water to the particular desired concentration.

About 20 *Lucilia cuprina* res. larvae are introduced into a test tube which contains approx. 1 cm$^3$ of horse meat and 0.5 ml of the preparation of active compound. After 24 hours, the degree of destruction is determined.

In this test, a highly pronounced activity is shown, for example, by the following compounds of the Preparation Examples: (1), (3), (7) and (8).

It is understood that the specification and examples are illustrative but not limitative of the present invention and that other embodiments within the spirit and scope of the invention will suggest themselves to those skilled in the art.

We claim:
1. A substituted pyrazoline derivative of the formula

$$\begin{array}{c} R^1 \quad R^2 \\ \phantom{R^1} \diagdown \phantom{R^2} \diagup R^3 \\ \text{structure with } R^4, R^5, R^6, W=C, N, H \end{array} \quad (I)$$

in which
R$^1$ represents optionally substituted phenyl or optionally substituted alkyl,
R$^2$ represents hydrogen, optionally substituted phenyl, optionally substituted alkyl or alkoxycarbonyl,
or R$^1$ and R$^2$ together represent an optionally benzofused alkylene radical,
R$^3$ represents hydrogen or alkyl,
R$^4$ represents hydrogen, optionally substituted phenyl or optionally substituted alkyl,
R$^5$ represents hydrogen or optionally substituted alkyl,
R$^6$ represents halogenoalkyl or halogenoalkoxy, and
W represents oxygen or sulphur.

2. A substituted pyrazoline derivative according to claim 1,
in which
R$^1$ represents phenyl which is optionally substituted by halogen, nitro, alkyl(C$_1$–C$_6$), alkoxy(C$_1$–C$_6$), halogenoalkyl(C$_1$–C$_6$), halogenoalkoxy(C$_1$–C$_6$), alkyl(C$_1$–C$_6$)sulphonyl or halogenoalkyl(C$_1$–C$_6$)sulphonyl, or represents alkyl(C$_1$–C$_6$) which is optionally substituted by halogen, alkoxy(C$_1$–C$_6$) or halogenoalkoxy(C$_1$–C$_6$),
R$^2$ represents hydrogen, or phenyl which is optionally substituted by halogen, nitro, alkyl(C$_1$–C$_6$), alkoxy(C$_1$–C$_6$), halogenoalkyl(C$_1$–C$_6$), halogenoalkoxy(C$_1$–C$_6$), alkyl(C$_1$–C$_6$)sulphonyl or halogenoalkyl(C$_1$–C$_6$)sulphonyl, or represents alkyl(C$_1$–C$_6$) which is optionally substituted by halogen, alkoxy(C$_1$–C$_6$) or halogenoalkoxy(C$_1$–C$_6$), or represents alkoxy(C$_1$–C$_6$)carbonyl,
R$^3$ represents hydrogen or alkyl(C$_1$–C$_6$),
R$^4$ represents hydrogen, or phenyl which is optionally substituted by halogen, alkoxy(C$_1$–C$_4$), alkyl(C$_1$–C$_4$), halogenoalkyl(C$_1$–C$_4$) or halogenoalkoxy(C$_1$–C$_4$), or represents alkyl(C$_1$–C$_6$) which is optionally substituted by halogen or alkoxy(C$_1$–C$_4$),
R$^5$ represents hydrogen or alkyl(C$_1$–C$_6$) which is optionally substituted by halogen or alkoxy(C$_1$–C$_4$),
R$^6$ represents halogenoalkyl(C$_1$–C$_6$) or halogenoalkoxy(C$_1$–C$_6$)
and
W represents oxygen or sulphur.

3. A substituted pyrazoline derivative according to claim 1,
in which
R$^1$ represents phenyl which is optionally substituted by fluorine, chlorine, bromine, nitro, alkyl(C$_1$–C$_4$), alkoxy(C$_1$–C$_4$), halogenoalkyl(C$_1$–C$_4$), halogenoalkoxy(C$_1$–C$_4$), alkyl(C$_1$–C$_4$)sulphonyl, halogenoalkoxy(C$_1$–C$_4$)sulphonyl or halogenoalkoxy($C_1$–$C_4$)sulphonyl, or represents alkyl($C_1$–$C_4$) which is optionally substituted by fluorine, chlorine, bromine, alkoxy($C_1$–$C_4$), or halogenoalkoxy($C_1$–$C_4$), $R^2$ represents hydrogen, or phenyl which is optionally substituted by fluorine, chlorine, bromine, nitro, alkyl($C_1$–$C_4$), alkoxy($C_1$–$C_4$), halogenoalkyl($C_1$–$C_4$), halogenoalkoxy($C_1$–$C_4$), alkyl($C_1$–$C_4$))sulphonyl or halogenoalkyl($C_1$–$C_4$)sulphonyl, or represents alkyl($C_1$–$C_4$) which is optionally substituted by fluorine, chlorine, bromine, alkoxy($C_1$–$C_4$) or halogenoalkoxy($C_1$–$C_4$), or represents alkoxy($C_1$–$C_4$)carbonyl, $R^3$ represents hydrogen or alkyl($C_1$–$C_4$), $R^4$ represents hydrogen, or phenyl which is optionally substituted by fluorine, chlorine, bromine, methoxy, ethoxy, methyl, ethyl, halogenoalkyl($C_1$–$C_2$) or halogenoalkoxy($C_1$–$C_2$), or represents alkyl($C_1$–$C_4$) which is optionally substituted by fluorine, chlorine, bromine, methoxy or ethoxy, $R^5$ represents hydrogen, or alkyl($C_1$–$C_4$) which is optionally substituted by fluorine, chlorine, bromine, methoxy or ethoxy, $R^6$ represents halogenoalkyl which has 1 to 4 carbon atoms and 1 to 7 identical or different halogen atoms from the group consisting of fluorine, chlorine and bromine, or represents halogenoalkoxy which has 1 to 4 carbon atoms and 1 to 7 identical or different halogen atoms from the group consisting of fluorine, chlorine and bromine, and W represents oxygen or sulphur.

4. A substituted pyrazoline derivative according to claim 1,
in which
$R^1$ represents phenyl which is optionally substituted by fluorine, chlorine, bromine, nitro, methyl, ethyl, methoxy, ethoxy, halogenoalkyl which has 1 to 4 carbon atoms and 1 to 7 identical or different halogen atoms from the group consisting of fluorine, chlorine and bromine, or by halogenoalkoxy which has 1 to 4 carbon atoms and 1 to 7 identical or different halogen atoms from the group consisting of fluorine, chlorine and bromine, or by alkyl($C_1$–$C_2$)sulphonyl, halogenoalkyl($C_1$–$C_2$)sulphonyl which has 1 or 2 carbon atoms and 1 to 5 identical or different (halogen atoms from the group consisting of fluorine, chlorine and bromine, or by halogenoalkoxy($C_1$–$C_2$)sulphonyl which has 1 or 2 carbon atoms and 1 to 5 identical or different halogen atoms from the group consisting of fluorine, chlorine and bromine, or represents alkyl($C_1$–$C_3$) which is optionally substituted by fluorine, chlorine, methoxy, ethoxy or halogenoalkoxy($C_1$–$C_2$) which has 1 or 2 carbon atoms and 1 to 5 identical or different halogen atoms from the group consisting of fluorine, chlorine and bromine, $R^2$ represents hydrogen, or phenyl which is optionally substituted by fluorine, chlorine, bromine, nitro, methyl, ethyl, methoxy, ethoxy, halogenoalkyl which has 1 to 4 carbon atoms and 1 to 5 identical or different halogen atoms from the group consisting of fluorine, chlorine and bromine, or by halogenoalkoxy which has 1 to 4 carbon atoms and 1 to 7 identical or different halogen atoms from the group consisting of fluorine, chlorine and bromine, or by alkyl($C_1$–$C_3$)sulphonyl or halogenoalkyl($C_1$–$C_3$)sulphonyl, or represents alkyl($C_1$–$C_3$) which is optionally substituted by fluorine, chlorine, bromine, methoxy, ethoxy or halogenoalkoxy which has 1 to 4 carbon atoms and 1 to 7 identical or different halogen atoms from the group consisting of fluorine, chlorine and bromine, or represents alkoxy($C_1$–$C_3$)carbonyl, $R^3$ represents hydrogen, methyl or ethyl, $R^4$ represents hydrogen, or phenyl which is optionally substituted by fluorine, chlorine, methoxy, ethoxy, methyl, ethyl, halogenoalkyl which has 1 or 2 carbon atoms and 1 to 5 identical or different halogen atoms from the group consisting of fluorine, chlorine and bromine, or by halogenoalkoxy which has 1 or 2 carbon atoms and 1 to 5 identical or different halogen atoms from the group consisting of fluorine, chlorine and bromine, or represents alkyl($C_1$–$C_3$) which is optionally substituted by fluorine, chlorine, bromine, methoxy or ethoxy, $R^5$ represents hydrogen, or alkyl($C_1$–$C_3$) which is optionally substituted by fluorine, chlorine, methoxy or ethoxy, and $R^6$ represents trifluoromethyl, chloro-difluoromethyl, 2,2,2-trifluoroethyl, pentafluoroethyl, difluoromethyl, 1,2,2,2-tetrafluoroethyl, 1,1,2,3,3,3-hexafluoropropyl, trifluoromethoxy, chloro-difluoromethoxy, 2,2,2-trifluoroethoxy, pentafluoroethoxy, difluoromethoxy, 1,2,2,2-tetrafluoroethoxy or 1,1,2,3,3,3-hexafluoropropoxy.

5. A compound according to claim 1, wherein such compound is N-4-trifluoromethylcyclohexyl-3,4-bis-(4-chlorophenyl)-4,5-dihydro-1-pyrazolecarboxamide of the formula

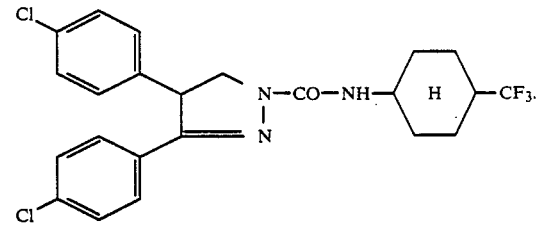

6. A compound according to claim 1, wherein such compound is N-4-trifluoromethylcyclohexyl-3-(4-difluoromethoxyphenyl)-4-phenyl-4,5-dihydro-1-pyrazolecarboxamide of the formula

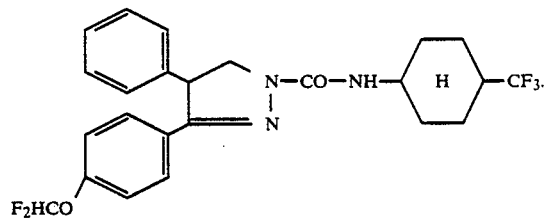

7. A compound according to claim 1, wherein such compound is N-3-trifluoromethylcyclohexyl-3,4-bis-(4-fluorophenyl)-4,5-dihydro-1-pyrazolecarboxamide of the formula

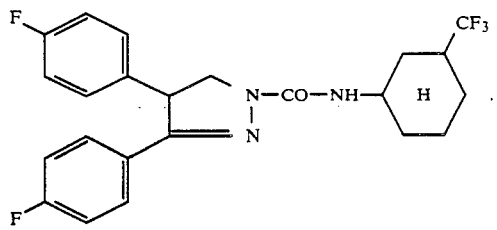

8. A compound according to claim 1, wherein such compound is N-4-trifluoromethylcyclohexyl-3,4-bis-(4-fluorophenyl)-4,5-dihydro-1-pyrazolecarboxamide of the formula

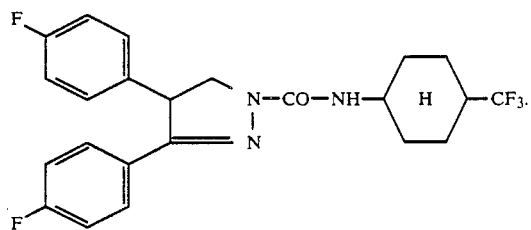

9. A compound according to claim 1, wherein such compound is N-4-trifluoromethylcyclohexyl-3,4-bis-(4-fluorophenyl)-4,5-dihydro-1-pyrazolethiocarboxamide of the formula

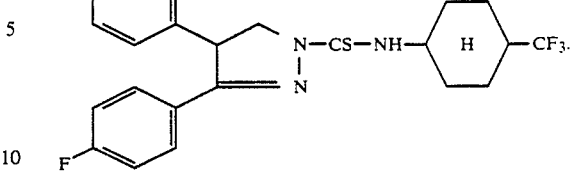

10. A compound according to claim 1, wherein such compound is N-4-trifluoromethylcyclohexyl-3,4-bis-(4-chlorophenyl)-4,5-dihydro-1-pyrazolethiocarboxamide of the formula

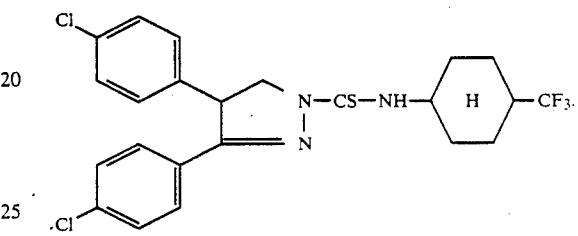

11. A pesticidal composition comprising a pesticidally effective amount of a compound according to claim 1 and a diluent.

12. A method of combating pests which comprises applying to such pests or to a locus from which it is desired to exclude such pests a pesticidally effective amount of a compound according to claim 1.

13. The method according to claim 12, wherein such compound is
N-4-trifluoromethylcyclohexyl-3,4-bis-(4-chlorophenyl)-4,5-dihydro-1-pyrazolecarboxamide,
N-4-trifluoromethylcyclohexyl-3-(4-difluoromethoxyphenyl)-4-phenyl-4,5-dihydro-1-pyrazolecarboxamide,
N-3-trifluoromethylcyclohexyl-3,4-bis-(4-fluorophenyl)-4,5-dihydro-1-pyrazolecarboxamide,
N-4-trifluoromethylcyclohexyl-3,4-bis-(4-fluorophenyl(-4,5-dihydro-1-pyrazolecarboxamide,
N-4-trifluoromethylcyclohexyl-3,4-bis-(4-fluorophenyl)-4,5-dihydro-1-pyrazolethiocarboxamide or
N-4-trifluoromethylcyclohexyl-3,4-bis-(4-chlorophenyl)-4,5-dihydro-1-pyrazolethiocarboxamide.

* * * * *